US012590537B2

(12) United States Patent
Swett

(10) Patent No.: US 12,590,537 B2
(45) Date of Patent: Mar. 31, 2026

(54) PIEZOELECTRIC LEAF CELL SENSOR ARRAY FOR MULTIPHASE GAS-OIL-WATER FLOW METERING

(71) Applicant: ARAMCO SERVICES COMPANY, Houston, TX (US)

(72) Inventor: Dwight W. Swett, Houston, TX (US)

(73) Assignee: SAUDI ARABIAN OIL COMPANY, Dhahran (SA)

(*) Notice: Subject to any disclaimer, the term of this patent is extended or adjusted under 35 U.S.C. 154(b) by 280 days.

(21) Appl. No.: 18/495,242

(22) Filed: Oct. 26, 2023

(65) Prior Publication Data

US 2025/0137370 A1    May 1, 2025

(51) Int. Cl.
  E21B 49/08     (2006.01)
  G01N 9/36     (2006.01)
    (Continued)

(52) U.S. Cl.
  CPC .......... E21B 49/08 (2013.01); E21B 49/0875 (2020.05); G01N 9/36 (2013.01);
    (Continued)

(58) Field of Classification Search
  CPC ....... E21B 49/08; E21B 49/0875; G01N 9/36; G01N 29/024; G01N 29/222;
    (Continued)

(56) References Cited

U.S. PATENT DOCUMENTS

| | | | |
|---|---|---|---|
| 4,240,285 A | 12/1980 | Langdon | |
| 7,146,857 B2* | 12/2006 | Hok ..................... G01N 29/222 |
| | | | 73/24.01 |

(Continued)

FOREIGN PATENT DOCUMENTS

| | | |
|---|---|---|
| WO | 2018017558 A1 | 1/2018 |
| WO | 2018089869 A1 | 5/2018 |
| WO | 2020128512 A1 | 6/2020 |

OTHER PUBLICATIONS

A. Chaudhuri et al., "An Algorithm for Determining Volume Fractions in Two-Phase Liquid Flows by Measuring Sound Speed", Journal of Fluids Engineering, Oct. 2012, vol. 134, pp. 101301-1-101301-7 (7 pages).

(Continued)

*Primary Examiner* — Jill E Culler
(74) *Attorney, Agent, or Firm* — Osha Bergman Watanabe & Burton LLP

(57) ABSTRACT

A fluid sensor device for measuring properties of a fluid is disclosed. The fluid sensor device includes a leaf cell sensor having a piezoelectric structure acting on a subdomain of the fluid that flows through the piezoelectric structure to create an intrinsic Helmholtz cavity response, and an enclosure enclosing the leaf cell sensor and including (i) a flowthrough shroud having an inlet that allows the fluid to enter the enclosure and pass across the leaf cell sensor, and a Helmholtz cavity wall that couples the intrinsic Helmholtz cavity response with an external acoustic field of the leaf sensor to increase a measurement sensitivity, (ii) a cylindrical housing having an outlet that allows the fluid to exit the enclosure, and (iii) a pressure feedthrough connector that transmits an electrical signal induced by the intrinsic Helmholtz cavity response to represent the properties of the fluid.

9 Claims, 11 Drawing Sheets

(51) Int. Cl.

| | |
|---|---|
| *G01N 29/024* | (2006.01) |
| *G01N 29/22* | (2006.01) |
| *G01N 29/24* | (2006.01) |
| *G01N 33/28* | (2006.01) |
| *H10N 30/80* | (2023.01) |
| *H10N 30/88* | (2023.01) |

(52) U.S. Cl.
CPC ......... *G01N 29/024* (2013.01); *G01N 29/222* (2013.01); *G01N 29/2437* (2013.01); *G01N 33/2823* (2013.01); *H10N 30/802* (2023.02); *H10N 30/886* (2023.02)

(58) Field of Classification Search
CPC ........... G01N 29/2437; G01N 33/2823; H01N 30/802; H01N 30/886
See application file for complete search history.

(56) References Cited

U.S. PATENT DOCUMENTS

| | | | |
|---|---|---|---|
| 7,994,932 | B2 | 8/2011 | Huang et al. |
| 9,173,600 | B2 | 11/2015 | Matsiev et al. |
| 10,018,034 | B2 | 7/2018 | Chronister |
| 11,035,771 | B2 | 6/2021 | Niedermayer |
| 11,066,930 | B2 | 7/2021 | Swett et al. |
| 11,428,100 | B2 | 8/2022 | Swett et al. |
| 11,536,679 | B2 | 12/2022 | Swett |
| 2002/0093348 | A1 | 7/2002 | Buhler et al. |
| 2003/0183383 | A1 | 10/2003 | Guerrero |
| 2004/0129056 | A1* | 7/2004 | Hok .......................... G01N 9/36 73/24.05 |
| 2014/0367092 | A1 | 12/2014 | Roberson et al. |
| 2016/0326866 | A1 | 11/2016 | Swett |
| 2018/0003027 | A1 | 1/2018 | Donzier et al. |
| 2018/0110913 | A1 | 4/2018 | Loderer et al. |
| 2019/0023589 | A1 | 1/2019 | Norman et al. |
| 2020/0355071 | A1 | 11/2020 | Maity |
| 2020/0355073 | A1 | 11/2020 | Maity et al. |
| 2021/0131990 | A1 | 5/2021 | Swett |
| 2021/0318219 | A1 | 10/2021 | Rutgers et al. |

OTHER PUBLICATIONS

G. T. Kuster et al., "Velocity and attenuation of seismic waves in two-phase media: Part I. Theoretical Formulations" Geophysics, Oct. 1974, vol. 39, No. 5, pp. 587-606 (20 pages).
G. Meng et al., "Composition measurements of crude oil and process water emulsions using thick-film unltrasonic transducers," Chemical Engineering and processing, 2006, vol. 45, pp. 383-391 (9 pages).
P. Moon et al., "Field Theory Handbook", 1988, Berlin: Springer-Verlag (244 pages).
C. Tsouris et al., "Volume fraction measurements of water in oil by an ultrasonic technique", Ind. Eng. Chem. Res., 1993, vol. 32, pp. 998-1002 (5 pages).
R. J. Urick, "A sound velocity method for determining the compressibility of finely divided substances", Journal of Applied Physics, 1947, pp. 983-987 (6 pages).

G. H. Roshani et al., "Volume fraction determination of the annular three-phase flow of gas-oil-water using adaptive neuro-fuzzy inference system", Comp. Appl. Math., 2018, pp. 4321-4341 (21 pages).
R. Ramos et al., "Volume Fraction Calculation in Multiphase System such as Oil-Water-Gas using Neutron" 2007 International Nuclear Atlantic Conference, 2007 (8 pages).
A. R. Nejad et al., "Improving the Measurement of Volume Fraction of Multiphase Fluids Based on Attenuation of Gamma Rays Without the Use of Artificial Intelligence" MAPAN Journal of Metrology Society of India, 2021, vol. 36, No. 4, pp. 869-874 (6 pages).
C. M. Salgado et al., "Three-phase flow meters based on X-rays and artificial neural network to measure the flow compositions" Flow Measurement and Instrumentation, 2021, vol. 8,10205 (7 pages).
D. W. Swett et al., "Experimental Characterization of a Piezoelectric Leaf-Cell Sensor for Simultaneous Fluid Density and Sound Speed Measurement", IEEE Sensors Letters, 2019, vol. 2, No. 3, pp. 1-4 (4 pages).
A. B. Wood, "A Textbook of Sound", London: G. Bell and Sons, 1930 (590 pages).
D. W. Swett et al., "Multiphase Gas-Oil-Water Flow Metering using Piezoelectric Leaf-Cell Sensor Array", IEEE Sensors Jounal, 2017, pp. 1-7 (7 pages).
J. Hoja and G. Lentka, "Fast Impedance Spectroscopy Method using Square Pulse Excitation," in 12th IMEKO TC1 & TC7 Joint Symposium on Man Science & Measurement, Annecy, 2008 (6 pages).
S. Sun, L. Xu, Z. Cao, H. Zhou and W. Yang, "A high-speed electrical impedance measurement circuit based on information-filtering demodulation," Measurement Science and Technology, vol. 25, p. 075010, 2014 (11 pages).
S. Majzoub, A. Allagui and A. S. Elwakil, "Fast Spectral Impedance Measurement Method Using a Structured Random Excitation," IEEE Sensors Journal, vol. 20, No. 15, p. 8637, 2020 (7 pages).
J. Sihvo, D.-I. Stroe, T. Messo and T. Roinila, "A Fast Approach for battery Impedance Identification Using Pseudo Random Sequence (PRS) Signals," IEEE Transactions on Power Electronics, vol. 35, No. 3, pp. 2548-2557, 2020 (12 pages).
First Examination Report issued in corresponding Saudi Arabian Application No. 522432468; dated Oct. 28, 2020 (9 pages).
Swett, Dwight et al., "Multiphase Flow Analysis Using Piezoelectric Leaf-Cell Sensor Array"; IEEE Sensors Letters; vol. 6, Issue 10, Article Sequence No. 2501104; Oct. 2022 (4 pages).
Non-Final Office Action issued by the U.S. Patent Office for corresponding U.S. Appl. No. 18/321,320, mailed Apr. 3, 2025 (10 pages).
International Search Report issued for corresponding international patent application No. PCT/US2024/051896, mailed Jan. 27, 2025 (6 pages).
Written Opinion issued for corresponding international patent application No. PCT/US2024/051896, mailed Jan. 27, 2025 (11 pages).
D. Swett, et al., "Multiphase Flow Analysis Using Piezoelectric Leaf-Cell Sensor Array," IEEE Sensors Council, 2022 (4 pages).
Munir Farasat et al., "A new method for wideband characterization of resonator-based sensing platforms", Review of Scienctific Instruments, Mar. 29, 2011, vol. 82, No. 3, pp. 035119.1-035119.8 (8 pages).
International Search Report and Written Opinion issued in International Application No. PCT/US2024/029431, dated Sep. 5, 2024 (14 pages).

* cited by examiner 6.7" Casing ID 9.5" Casing ID

PIEZOELECTRIC LEAF CELL SENSOR ARRAY FOR MULTIPHASE GAS-OIL-WATER FLOW METERING

BACKGROUND

Generally, fluids in the petrochemical industry, for example, fluids in a wellbore of an oil field, may be single or multiphase fluids. Wellbore fluids may include mixtures of miscible and immiscible fluids, for example, mixtures of oil and water. Wellbore fluids may include mixtures of liquid and gas, liquid and solid, gas and solid, or mixtures of liquid, gas, and solid. Environmental conditions in a wellbore and in fluid systems associated with the extraction and transport of hydrocarbons may vary significantly. For example, temperatures in a wellbore may vary from approximately 2° C. to over 130° C. Pressures may vary from atmospheric pressure to over (50) Megapascals (MPa) at the bottom of an oil well. Composition of a wellbore fluid and environmental conditions in a wellbore greatly affect the rheological properties of a fluid. Analysis of rheological properties in situ may be important to ensure proper handling of fluids in a wellbore and related fluid systems. For example, if a wellbore fluid exhibits a viscosity above a certain threshold value, mitigating measures may need to be taken to maximize the degree of fluid extraction. Such measures include thermal methods (for example, hot fluid circulation), pressure management (for example, pumping or boosting), or chemical treatments. Because these measures may be costly, accurate determination of wellbore fluid properties is critical.

During oil and gas operations, it is often difficult to determine fluid properties in a downhole well due to inaccessibility, contamination of fluids, mixing of fluids, and the like. As a result, typical operations deploy multiple tools that may be specialized to determine a single fluid property, such as density. These tools are often fragile, and as a result, may not be utilized in multiple operations. Furthermore, installing multiple tools along a drill or wireline string increases costs of the operation and also may lead to slower drilling and/or wireline logging operations because some tools are individually tripped into and out of the well.

SUMMARY

In general, in one aspect, the invention relates to a fluid sensor device for measuring one or more properties of a fluid. The fluid sensor device includes a leaf cell sensor comprising a piezoelectric structure acting on a subdomain of the fluid that flows through the piezoelectric structure to create an intrinsic Helmholtz cavity response, and an enclosure enclosing the leaf cell sensor and comprising (i) a flowthrough shroud comprising an inlet that allows the fluid to enter the enclosure and pass across the leaf cell sensor, and a Helmholtz cavity wall that couples the intrinsic Helmholtz cavity response with an external acoustic field of the leaf sensor to increase a measurement sensitivity of the fluid sensor device, (ii) a cylindrical housing comprising an outlet that allows the fluid to exit the enclosure, and (iii) a pressure feedthrough connector that transmits an electrical signal induced by the intrinsic Helmholtz cavity response from the piezoelectric structure of the leaf cell sensor, wherein the electrical signal represents the one or more properties of the fluid.

In general, in one aspect, the invention relates to a fluid analysis tool for measuring one or more properties of a fluid. The fluid analysis tool includes an axial spring and a plurality of arms movable, in response to extension of the axial spring, from a retracted position into an expanded position, each arm comprising at least one fluid sensor device for measuring one or more properties of a fluid, wherein the at least one fluid sensor device comprises a leaf cell sensor comprising a piezoelectric structure acting on a subdomain of the fluid that flows through the piezoelectric structure to create an intrinsic Helmholtz cavity response and an enclosure enclosing the leaf cell sensor and comprising (i) a flowthrough shroud comprising an inlet that allows the fluid to enter the enclosure and pass across the leaf cell sensor, and a Helmholtz cavity wall that couples the intrinsic Helmholtz cavity response with an external acoustic field of the leaf sensor to increase a measurement sensitivity of the fluid sensor device, (ii) a cylindrical housing comprising an outlet that allows the fluid to exit the enclosure, and (iii) a pressure feedthrough connector that transmits an electrical signal induced by the intrinsic Helmholtz cavity response from the piezoelectric structure of the leaf cell sensor, wherein the electrical signal represents the one or more properties of the fluid.

In general, in one aspect, the invention relates to system for performing a wellbore operation. The system includes a wellbore penetrating a formation, a work string conveyed in the wellbore, and a fluid analysis tool suspended in the wellbore via the work string for measuring one or more properties of a fluid in the wellbore to facilitate the wellbore operation, wherein the fluid analysis tool comprises an axial spring and a plurality of arms movable, in response to extension of the axial spring, from a retracted position into an expanded position, each arm comprising at least one fluid sensor device for measuring one or more properties of a fluid, wherein the at least one fluid sensor device comprises a leaf cell sensor comprising a piezoelectric structure acting on a subdomain of the fluid that flows through the piezoelectric structure to create an intrinsic Helmholtz cavity response, and an enclosure enclosing the leaf cell sensor and comprising (i) a flowthrough shroud comprising an inlet that allows the fluid to enter the enclosure and pass across the leaf cell sensor, and a Helmholtz cavity wall that couples the intrinsic Helmholtz cavity response with an external acoustic field of the leaf sensor to increase a measurement sensitivity of the fluid sensor device, (ii) a cylindrical housing comprising an outlet that allows the fluid to exit the enclosure, and (iii) a pressure feedthrough connector that transmits an electrical signal induced by the intrinsic Helmholtz cavity response from the piezoelectric structure of the leaf cell sensor, wherein the electrical signal represents the one or more properties of the fluid.

All or parts of the methods, systems, and techniques described in this specification may be implemented as a computer program product. The computer program product may include instructions that are stored on one or more non-transitory machine-readable storage media. The instructions may be executable on more or more processing devices. The example apparatus or example methods may be used with a multiphase fluid. The example apparatus or example methods may be used with a wellbore fluid.

Any two or more of the features described in this specification, including in this summary section, may be combined to form implementations not specifically described in this specification.

The details of one or more implementations are set forth in the accompanying drawings and the description. Other features and advantages will be apparent from the description and drawings, and from the claims.

BRIEF DESCRIPTION OF THE DRAWINGS

Specific embodiments of the disclosed technology will now be described in detail with reference to the accompanying figures. Like elements in the various figures are denoted by like reference numerals for consistency.

DETAILED DESCRIPTION

Figure 1:
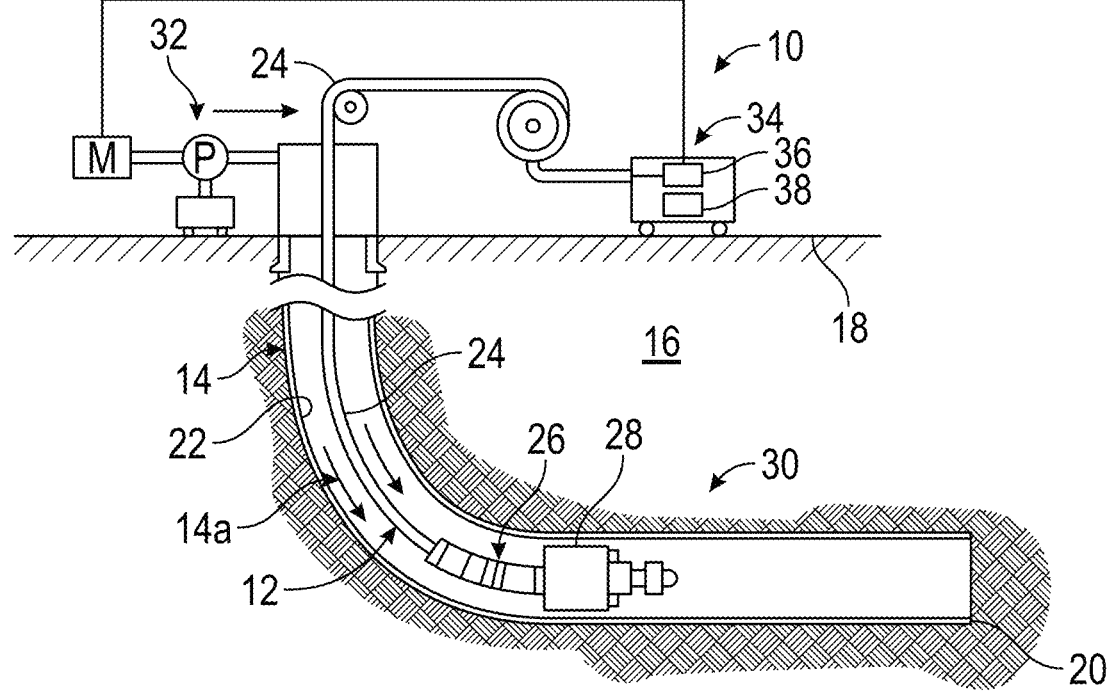
FIG. 1 is a schematic side view of an embodiment of a wireline system, in accordance with embodiments of the present disclosure.

In the following detailed description of embodiments of the disclosure, numerous specific details are set forth in order to provide a more thorough understanding of the disclosure. However, it will be apparent to one of ordinary skill in the art that the disclosure may be practiced without these specific details. In other instances, well-known features have not been described in detail to avoid unnecessarily complicating the description.

Throughout the application, ordinal numbers (e.g., first, second, third, etc.) may be used as an adjective for an element (i.e., any noun in the application). The use of ordinal numbers is not to imply or create any particular ordering of the elements nor to limit any element to being only a single element unless expressly disclosed, such as using the terms "before", "after", "single", and other such terminology. Rather, the use of ordinal numbers is to distinguish between the elements. By way of an example, a first element is distinct from a second element, and the first element may encompass more than one element and succeed (or precede) the second element in an ordering of elements.

Conventional methods for measurement of either fluid density or of fluid sound speed in unknown multi-phase fluids rely on an a priori knowledge of the mass density of the continuous and dispersed phases of the flow, and are not applicable to in-situ downhole applications since the mass densities of the components of the flow are not generally known and are only estimable from surface "dead oil" properties that do not account for effects such as downhole pressure, temperature, and gas-saturation. In addition, conventional methods utilize two separate measurements of two non-identical fluid domains, say M1-domain and M2-domain, to obtain measurements for fluid sound speed in M1-domain and fluid mass density in M2-domain. In the general no correlation can be proven to exist between the sound speeds and/or the mass densities of the two domains except in random occurrences.

To determine chemometric correlations between multi-phase fluid properties (such as volume fractions, gas-oil-ratio [GOR], API, live-oil density, live-oil sound speed, and live-oil compressibility) and the composite fluid acoustic properties of sound speed, bulk modulus and acoustic impedance, the measurements for sound speed and density of the composite fluid flow must be obtained in a specific congruent manner. That is, from a single measurement domain with a sensing field of interaction that is simultaneous and congruent relative to all the acoustic measurements and all the continuous/dispersed particles. Simultaneous and congruent measurements provides a true measure of the bulk composite fluid density and sound speed that have correlations with compositional and chemical properties of the bulk fluid.

In order to examine the correlations that may exist between the various compositional properties of liquid-liquid flows and the bulk fluid acoustic properties of the mixtures, an ideal acoustic impedance sensor that can measure simultaneously and congruently fluid density and sound speed properties is needed. Further, it is tacitly required that the sensor measurement attained provide delineated bulk fluid properties estimates of mass density and sound speed that can be discriminated directly from the measurement without any a priori knowledge of or assumption with regard to elemental properties of the bulk composite fluid.

Embodiments provides a fluid analysis tool, which is a downhole multi-measurement array instrument based on a leaf cell piezoelectric resonator that provides simultaneous and congruent downhole measurement of both fluid mass density and sound speed as well as velocity of the downhole fluid flow. The fluid analysis tool is amenable to a variety of configurations, including a combination of sensors in an array distributed throughout the borehole cross section to analyze multi-phase stratified and emulsified production flows such as encountered in highly-deviated and horizontal wellbores.

In one or more embodiments, the fluid analysis tool includes a leaf cell sensor enclosed by an enclosure. The leaf cell sensor has a piezoelectric structure acting on a subdomain of fluid that flows through the piezoelectric structure to create an intrinsic Helmholtz cavity response. The enclosure includes a flowthrough shroud, a cylindrical housing, and a pressure feedthrough connector. The flowthrough shroud has (i) an inlet that allows the fluid to enter the enclosure and pass across the leaf cell sensor and (ii) a Helmholtz cavity wall that couples the intrinsic Helmholtz cavity response with an external acoustic field of the leaf sensor to increase a measurement sensitivity of the fluid sensor device. The cylindrical housing has an outlet that allows the fluid to exit the enclosure. The pressure feedthrough connector transmits an electrical signal induced by the intrinsic Helmholtz cavity response from the piezoelectric structure of the leaf cell sensor where the electrical signal represents one or more properties of the fluid that are measured by the fluid analysis tool.

In one or more embodiments, the fluid analysis tool includes a sensor flow through shroud, a six-bar articulation mechanism, and passive deployment axial spring. The sensor flow through shroud provide protection against direct exposure to the downhole fluid flow constituents that may quickly damage the sensors due to the fragile nature of piezoelectric and optical components. The passive deployment axial spring eliminates the need for an active articulation device such as a hydraulic or electric motor and gear-drive.

FIG. 1 is a schematic elevation view of an embodiment of a wellbore system (10) that includes a work string (12) shown conveyed in a wellbore (14) formed in a formation (16) from a surface location (18) to a depth (20). The wellbore (14) is shown lined with a casing (22); however it should be appreciated that in other embodiments the wellbore (14) may not be cased. In various embodiments, the work string (12) includes a conveying member (24), such as an electric wireline, and a downhole tool or assembly (26) (also referred to as the bottomhole assembly or "BHA") attached to the bottom end of the wireline. The illustrated downhole assembly (26) includes various tools, sensors, measurement devices, communication devices, and the like, which will not all be described for clarity. In various embodiments, the downhole assembly (26) includes a measurement module (28), which will be described below, determining one or more properties of the formation (16). In the illustrated embodiment, the downhole tool measurement module (28) is arranged in a horizontal or deviated portion (30) of the wellbore (14), however it should be appreciated that the downhole tool measurement module (28) may also be deployed in substantially vertical segments of the wellbore (14).

The illustrated embodiment further includes a fluid pumping system (32) at the surface (18) that includes a motor that drives a pump to pump a fluid from a source to create a fluid flow (14a) into the wellbore (14) via a supply line or conduit. To control the rate of travel of the downhole assembly, tension on the wireline (12) is controlled at a winch on the surface. Thus, the combination of the fluid flow rate and the tension on the wireline may contribute to the travel rate or rate of penetration of the downhole assembly (16) into the wellbore (14). The wireline may be an armored cable that includes conductors for supplying electrical energy (power) to downhole devices and communication links for providing two-way communication between the downhole tool and surface devices. In aspects, a controller (34) at the surface is provided to control the operation of the pump and the winch to control the fluid flow rate into the wellbore and the tension on the wireline (12). In aspects, the controller (34) may be a computer-based system that may include a processor (36), such as a microprocessor, a storage device (38), such as a memory device, and programs and instructions, accessible to the processor for executing the instructions utilizing the data stored in the memory (38).

As described above, the illustrated embodiment includes the measurement module (28). As will be described below, in various embodiments, the measurement module (28) may include one or more piezoelectric helm resonators for determination of various fluid properties within the wellbore (14). For example during a production operation of the wellbore (14), oil and gas products may enter an annulus and flow along the BHA (26). In another example during a drilling operation of the wellbore (14), drilling fluid (i.e., mud) may circulate the wellbore (14) and flow along the BHA (26). The production operation, drilling operation, and other wellbore related operations are referred to as a wellbore operation. In these wellbore operations, at least a portion of that flow may be redirected into the measurement module (28). Within the measurement module (28), or proximate the measurement module (28) in certain embodiments, one or more fluid properties may be measured to facilitate wellbore operations. Furthermore, it should be appreciated that while various embodiments include the measurement module (28) incorporated into a wireline system, in other embodiments the measurement module (28) may be associated with rigid drill pipe, coiled tubing, or any other downhole exploration and production method.

Figure 2A:
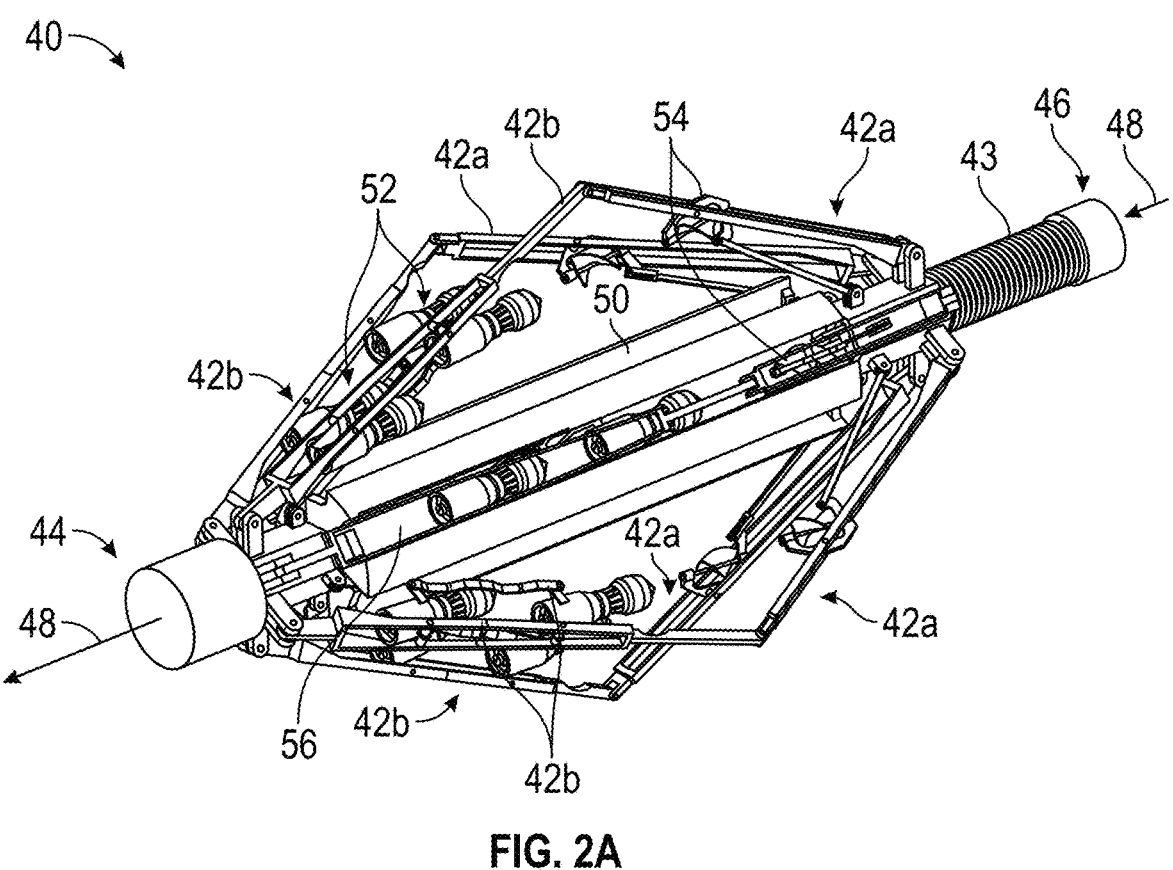
FIG. 2A illustrates a perspective view of a fluid analysis tool in an expanded position, in accordance with example embodiments.
Figure 2B:
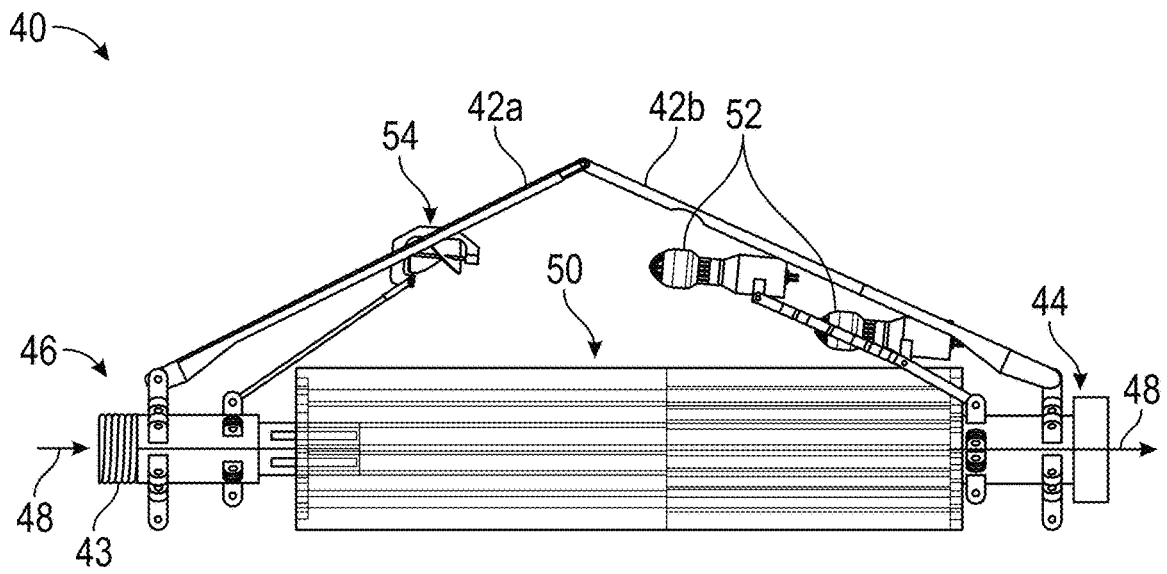
FIG. 2B illustrates a cross-sectional view of a fluid analysis tool in an expanded position, in accordance with example embodiments.

In some embodiments, the measurement module (28) includes a fluid analysis tool. FIGS. 2A and 2B illustrate a perspective view and a cross-sectional view, respectively of a fluid analysis tool (40) in an expanded position, in accordance with example embodiments. As illustrated, in some embodiments, the fluid analysis tool (40) includes a plurality of arms (42a, 42b) movable from a retracted position into an expanded position. In some embodiments, the plurality of arms (42a, 42b) are fixed at opposing ends (44, 46) and bendable at least one location (e.g., pivot) between the opposing ends (44, 46). The plurality of arms (42a, 42b) are arranged about a central axis (48) of the system, such that the plurality of arms (42a, 42b) expand away from the central axis (48) to move into the expanded position and contract towards the central axis (48) to position into the retracted position. In some embodiments, the tool (40) may include a central body (50) substantially align with the central axis (48). The central body (50) may be configured to receive or store the plurality of arms (42a, 42b) in the retracted position. In some embodiments, the central body (50) may include recessed portions (56) for receiving the arms and may include additionally recessed portions for receiving the fluid sensors (52) and/or flow spinners (54) on the arms (42a, 42b). An example of the fluid sensors (52) is described in FIGS. 5A-5D below.

The sensors (52, 54) may be coupled to the respective arms (42a, 42b) via a pivot and configured to swing inwardly away from the respective arms (42a, 42b) towards a central axis (48) or central body (50) of the tool (40). Alternatively, in some embodiments, the sensors (52, 54) may be configured to swing outward away from the respective arms (42a, 42b) and away from the central body (50) or to the side in a direction tangential to a central axis (48) of the tool (40). The fluid sensors (52, 54) may be movable from a stored position to a deployed position relative to the respective arms (42a, 42b). In the stored position, the sensors (52, 54) may be stored in the arms (42a, 42b). In the deployed position, the sensors (52, 54) are extended out from the arms (42a, 42b) and positioned substantially parallel to the axis of the borehole. In some embodiments, the sensors (52, 54) are at an angle within certain degrees from an axis of a borehole in which the tool (40) is positioned. Each endpoint of the six-bar mechanism as well as the four-bar mechanism includes a rotatable pivot. Thus, the sensors (52, 54) are positioned to substantially face the direction of fluid flow through the borehole.

In the illustrated example embodiments, the fluid analysis tool (40) includes six pairs of arms (42a, 42b), with two fluid sensors (52) integrated into each arm (42b) and one spinner (54) integrated into each arm (42a). Based on the fluid sensors (52) and spinners (54), the tool (40) provides simultaneous and congruent measurement of both downhole fluid density and sound speed (when downhole pressure is more than the multiphase bubble point pressure) as well as borehole fluid flow velocity. The measurement of the fluid properties and flow velocity is conducted in a distribution covering the wellbore cross-section by articulation of the array arms (42a, 42b) over a range of deployment angles, using the array of twelve fluid ID sensors (54) and six flow rate spinner sensors (52). The deployment of the tool (40) into the wellbore (14) articulates the fluid identification sensors (54) (e.g., leaf cell resonators) on a set of Stephenson six-bar mechanisms of the arms (42b), and the flow rate sensors (spinners) (52) on a set of four-bar mechanisms of the arms (42a) that maintain the orientation of each sensor (52, 54) to the borehole axis within ±3 degrees regardless of array deployment diameter, as described in the graph of FIG. 4 below. In particular, each sensor (52, 54) is attached to the six-bar mechanism or four-bar mechanism using two pivots. In mechanics, four-bar mechanism is the simplest closed-chain movable linkage that consists of four bodies, referred to as bars or links, connected in a loop by four joints. Generally, the joints are configured so that the links move in parallel planes. A six-bar mechanism is a linkage with one degree of freedom that is constructed from six links and seven joints. The six-bars and seven joints of the Stephenson linkage include one four-bar loop and one five-bar loop and have two ternary links that are separated by a binary link. Other pivoting or positioning mechanism may be employed to achieve the same or similar movement dynamics.

Based on the Stephenson six-bar mechanisms and the four-bar mechanisms of the fluid sensor tool (40), as the measurement module (28) with the fluid analysis tool (40) traverses various portions of the wellbore (14) depicted in FIG. 1 above, the central axis (48) of the sensors (52, 54) generally aligns with the borehole axis and remains parallel to the downhole fluid flow (14a). In particular, the arrow-head of the central axis (48) in FIG. 3 indicates the downstream side of the fluid flow (14a).

Figure 3A:
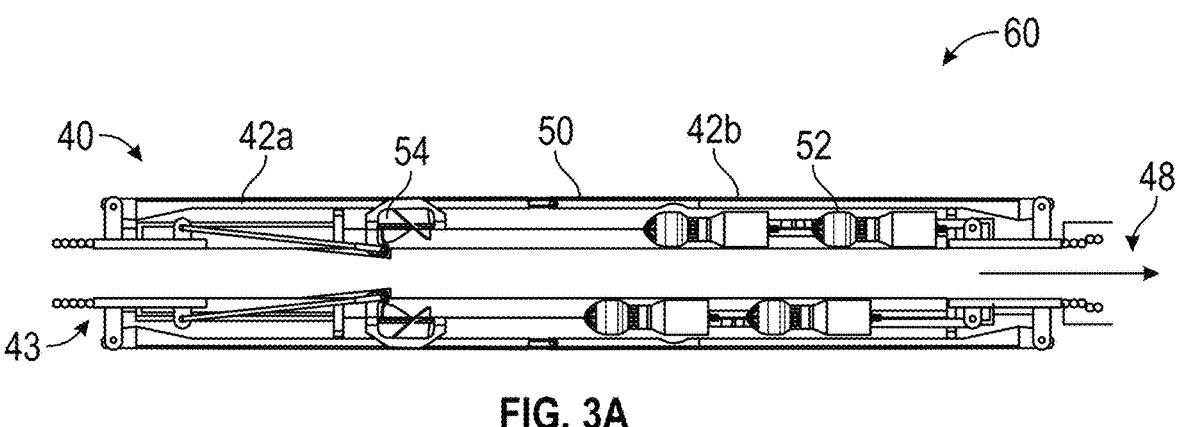
FIG. 3A illustrates the fluid analysis tool in the retracted position, in accordance with example embodiments.

FIG. 3A illustrates the fluid analysis tool (40) in the retracted position (60), in accordance with example embodiments. As mentioned, in some embodiments, the plurality of arms (42a, 42b) are arranged about a central body (50) of the tool (40). The central body (50) may be configured to receive or store the plurality of arms (42a, 42b) in the retracted position. Each of the arms (42a, 42b) may be the same length as the receiving portion of the central body (50) such that each arm (42) may be substantially flush against the central body (50), creating the minimum circumference of the tool (40). The fluid analysis tool may be lowered downhole in the contracted position and then deployed into an expanded position.

Figure 3B:
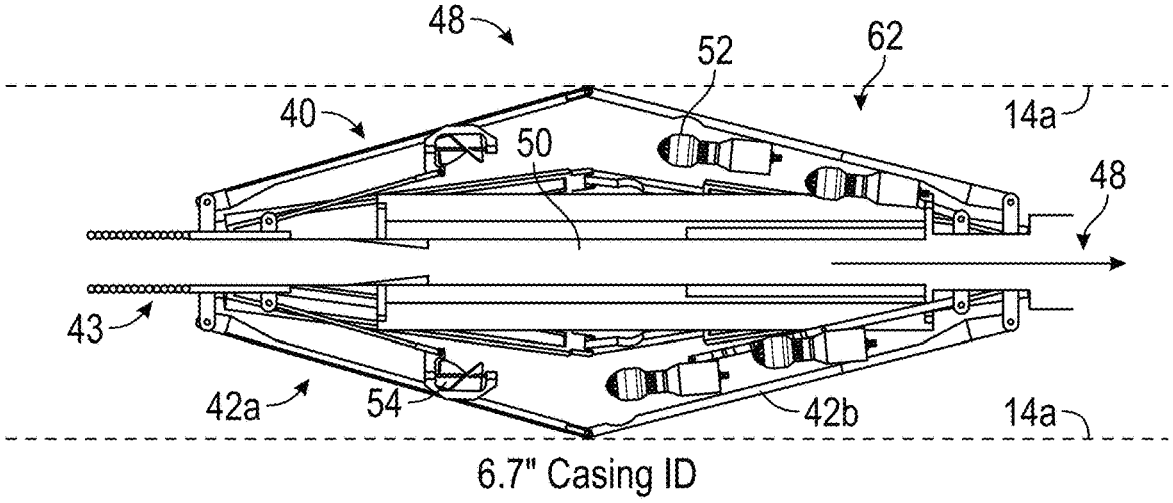
FIG. 3B illustrates the fluid analysis tool in a first expanded position, in accordance with example embodiments.
Figure 3C:
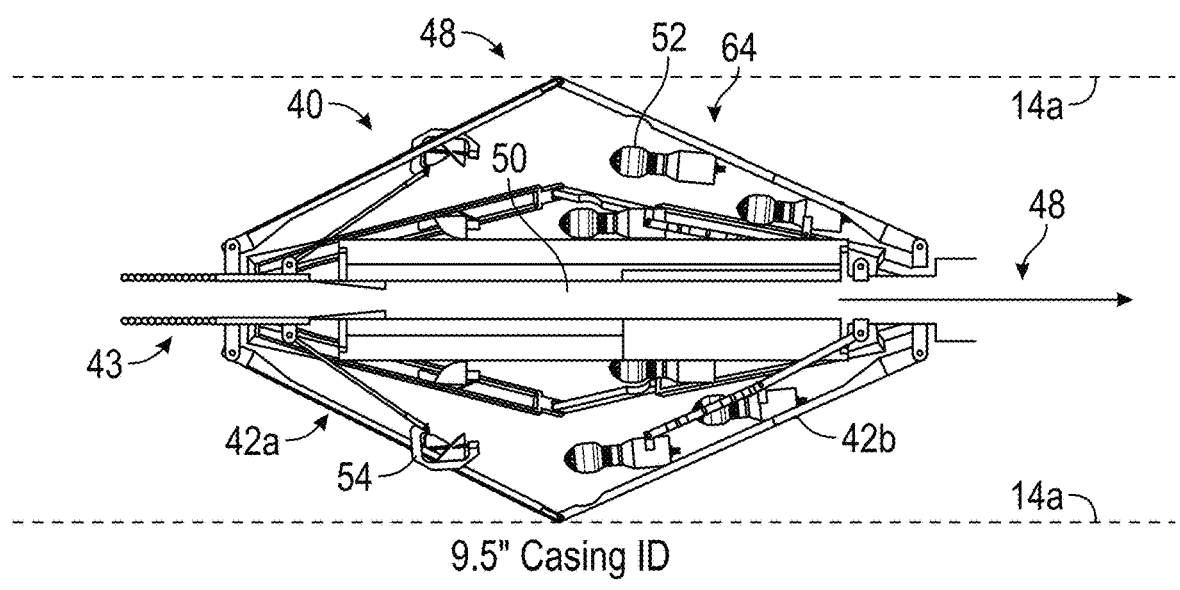
FIG. 3C illustrates the fluid analysis tool in a second expanded position, in accordance with example embodiments.

FIG. 3B illustrates the fluid analysis tool (40) in a first expanded position (62), in accordance with example embodiments. For example, this position may be used for deployment in a 6.7" casing. As illustrated, in the first expanded position (62), each of the arms (42a, 42b) bends outward, putting the arms (42a, 42b) at an angle with respect to the central body (50). The fluid sensors (52) and flow spinners (54) are also deployed out from the arms (42a, 42b) at an angle from the respective arm (42a, 42b). FIG. 3C illustrates the fluid analysis tool in a second expanded position (64), in which the arms (42a, 42b) expand further outward than in the first expanded position (62). For example, this position may be used for deployment in a 9.5" casing. Similar to the first expanded position (62), in the second expanded position (64), each of the arms (42a, 42b) bends outward at an angle and the fluid sensors (52) and flow spinners (54) are deployed out from the arms (42a, 42b). In the second expanded position (64), the arms (42a, 42b) are at a larger angle from the central body (50). However, the fluid sensors (52) and flow spinners (54) also deploy at a larger angle from the arms (42a, 42b), compensating for the larger angle between the arms (42a, 42b) and the central body (50). Thus, the fluid sensors (52) and flow spinners (54) are maintained at a minimal angle from the central body (50) or central axis (48) of the tool (40). As mentioned, the tool (40) may be designed to maintain the fluid sensors (52) and flow spinners (54) within ±3 degrees orientation to the borehole axis. Various embodiments and implementations of the tool may allow for different ranges. For example, some embodiments may be rated for ±2 degrees, ±10 degrees, etc.

In some embodiments, the fluid analysis tool (40) is deployable out to a 9.5" casing inner diameter. The arms (42a, 42b) are preloaded by a longitudinal compression spring (43) located concentric to the tool axis (48) which places the tool (40) in a normally fully expanded configuration depicted in FIGS. 2A-2B. As the tool (40) is deployed in decreasingly smaller borehole diameters, an actuation collar progressively compresses the preload spring (43), allowing the arms (42a, 42b) to passively retract to match the borehole and completion equipment inner diameter, as illustrated in the snapshots of FIGS. 3B-3C. The force of the compressed spring (43) balances the force of the arms (42a, 42b) against the inner wall (14a) of the wellbore (14). In particular, the longitudinal dimension (i.e., length) of the spring (43) progressively increases from FIG. 3A through FIG. 3B to FIG. 3C showing that the spring (43) extends along the axial direction of the fluid analysis tool (40) as the fluid analysis tool (40) traverses from a smaller diameter section of the borehole to progressively larger diameter sections of the borehole. The six-bar and four-bar mechanisms of the arms (42a, 42b) nest the fluid sensors (52) and spinners (54) in the central body (50) upon tool retraction, as shown in FIG. 3A

Figure 4:
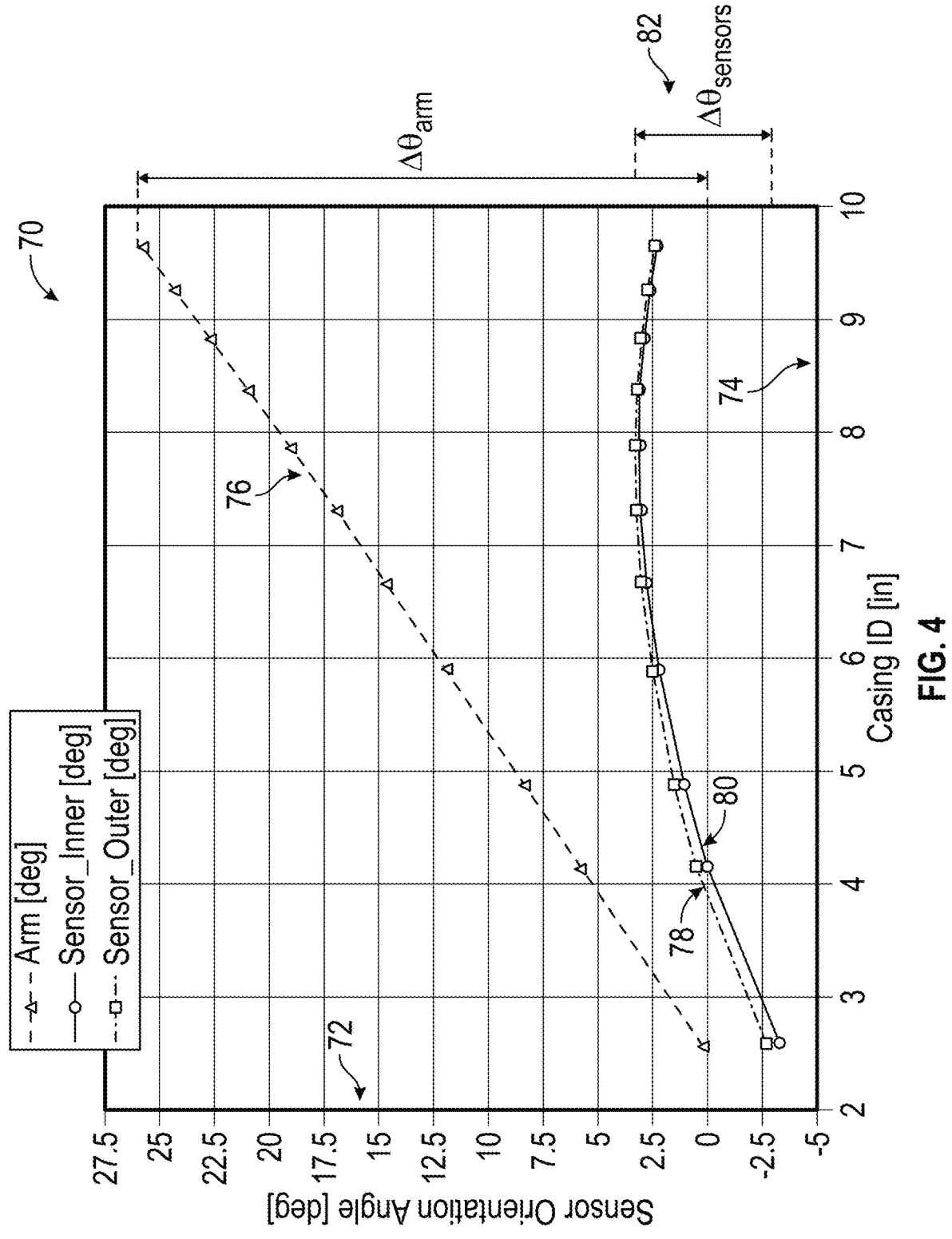
FIG. 4 is a graph illustrating the deployment angles of the arms, the fluid sensors, and the flow spinners with respect to the casing inner diameter, in accordance with example embodiments.
Figures 5A, 5B:
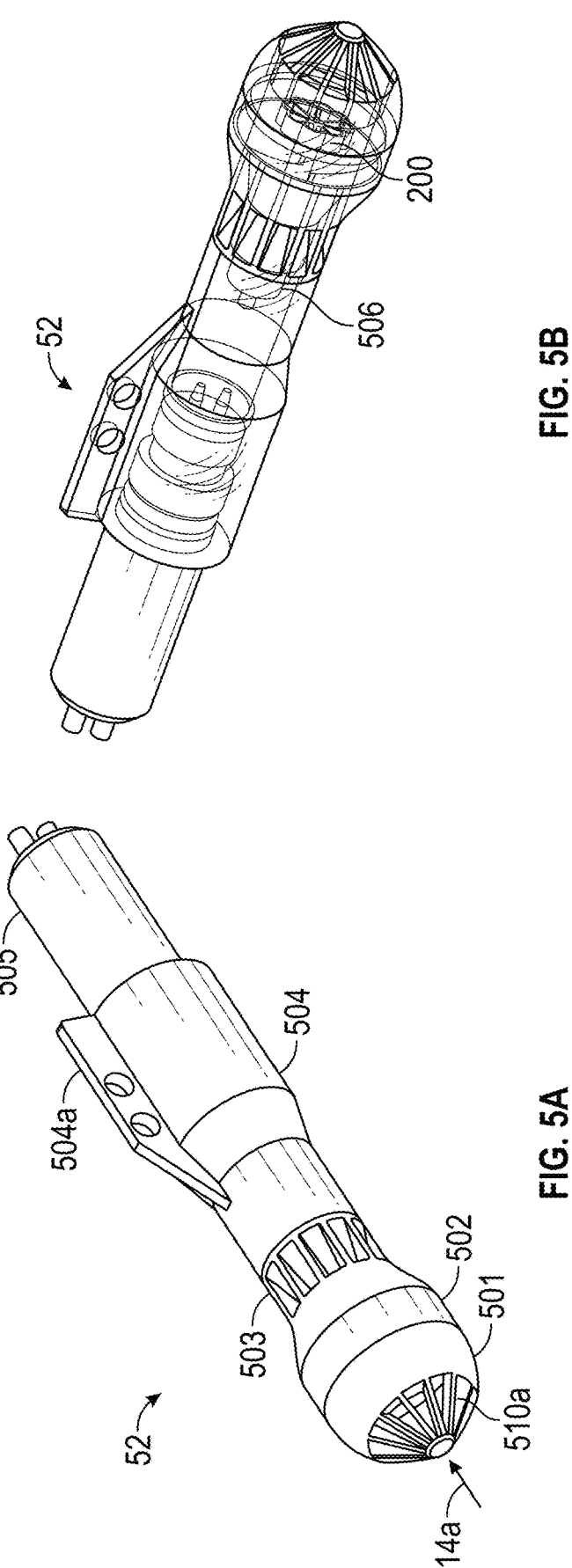
FIGS. 5A-5D show various views of an example fluid sensor based on a leaf cell resonator in accordance with one or more embodiments.
Figure 5C:
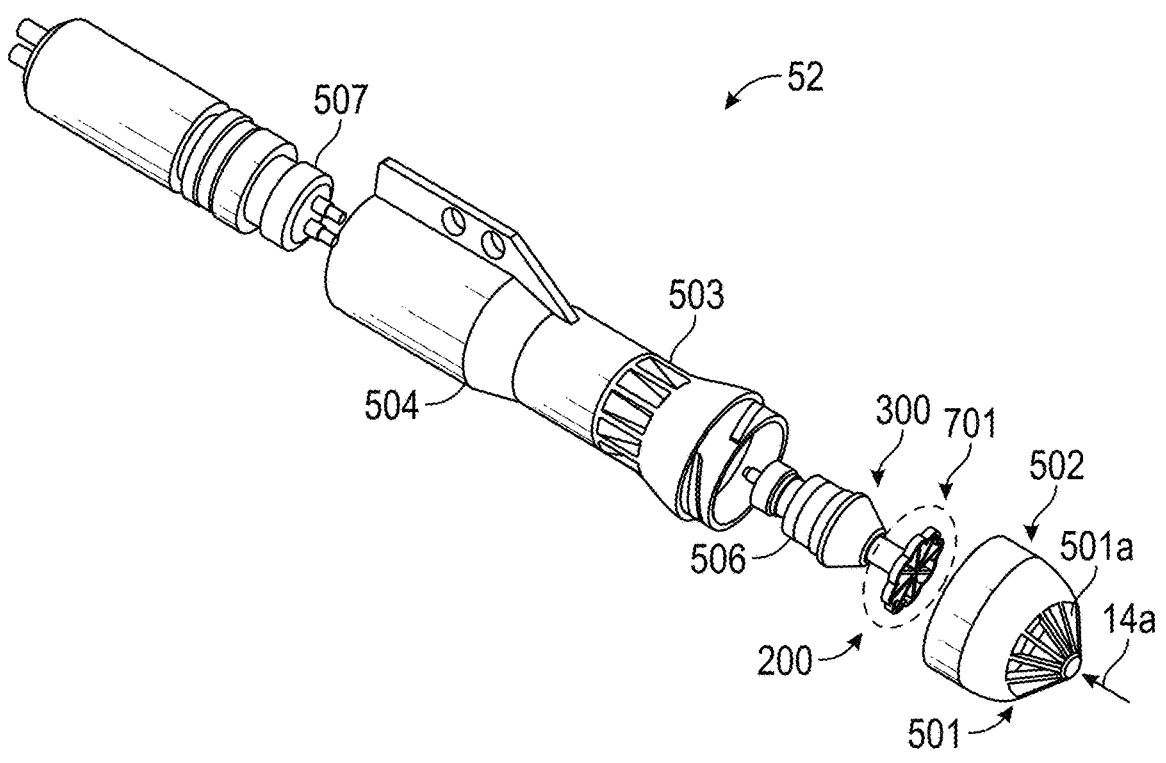
Figure 5D:
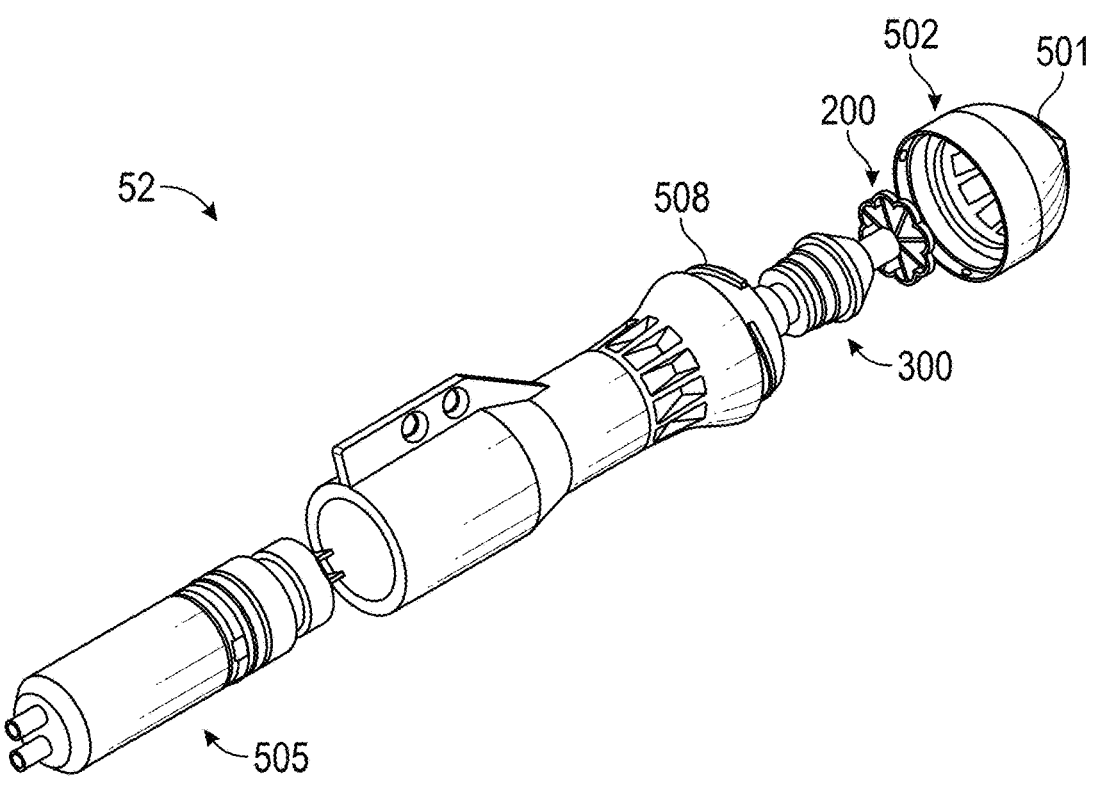

FIG. 4 is a graph (70) illustrating the deployment angle (76) of the arms (42a, 42b), deployment angle (78) of the fluid sensors (52), and deployment angle (80) of the flow spinners (54) with respect to the casing inner diameter. The deployment angle and the casing inner diameter correspond to the vertical axis (72) and the horizontal axis (74), respectively. As illustrated, the deployment angle (76) of the arms (42a, 42b) increases as the casing inner diameter increases when the arms (42a, 42b) expand further outward for larger boreholes. However, as the deployment angle (76) of the arms (42a, 42b) gets larger (i.e., tool (40) expands further outward), the deployment angle (78) of the fluid sensors (52) and deployment angle (80) of flow spinners (54) do not continue to increase accordingly. Rather, it stays within a range (82) of ±3 degrees regardless of the deployment angle (76) of the arms (42a, 42b).

FIGS. 5A-5D show various views of an example fluid sensor in accordance with one or more embodiments. As shown in FIGS. 5A-5D, the example fluid sensor (52) of the fluid analysis tool (40) is a sensor device that includes a leaf cell sensor assembly referred to as a leaf cell resonator (200) or simply a leaf cell (200).

Each leaf cell resonator (200) in the fluid sensor is integrated within an enclosure that includes a metal feed-through housing referred to as the pressure housing (504), a protective flowthrough shroud (501), and a pressure feed-through connector (507). The pressure housing (504) couples to the protective flowthrough shroud (501) and pressure feedthrough connector (507) at two opposite ends, for example via threaded connections such as the lock thread (508) to form the enclosure for the leaf cell resonator (200). A structure (504*a*) protrudes from the pressure housing (504) and provides at least a portion of a mounting mecha-nism (e.g., rotatable pivot, such as pin or any other suitable mechanism) to mechanically connect the fluid sensor device (52) to the arm (42*b*) as depicted in FIG. 1 above. The sensor output signals of the leaf cell resonator (200) is transmitted from the sensor coaxial feedthrough connector (506) coupled to a 2-pin pressure feedthrough connector (507) protected within a 2-pin pressure boot (505) before propa-gating through electrical wires embedded in articulating arms of the fluid analysis tool (40). The flowthrough shroud (501) includes an inlet (e.g., a pattern of radially directed openings (501*a*)) sized sufficiently large to allow rapid fluid flow (14*a*) across the leaf cell resonator (200) but sufficiently small to prevent impact damage to the leaf cell resonator (200) from large diameter solid particles in the flow stream. The fluid flow (14*a*) enters the enclosure for the leaf cell resonator (200) from the radially directed openings (501*a*) to pass across the leaf cell resonator (200) and exits the enclosure through an outlet, e.g., the flowthrough vents (503). The flowthrough vents (503) may include a ring of radially directed and slot-shaped openings in the pressure housing (504). To enhance the sensitivity of the leaf cell resonator (200) to fluid acoustic properties and improve the measurement for fluid density, an exterior metal Helmholtz cavity wall (502) is integrated in the flowthrough shroud structure to couple the leaf cell resonator (200) intrinsic interior Helmholtz resonator effect (referred to as the intrin-sic Helmholtz cavity response) with the leaf cell external acoustic field (701). In particular, the external acoustic field (701) is internal to the cavity wall (502), but external to the leaf-cell perimeter.

The addition of the exterior field-coupling Helmholtz cavity wall (502) increases the acoustic pressure field inter-nal and external of the piezoelectric leaf cell resonator (200). In this context, the flowthrough shroud (501) is referred to as a field-coupling Helmholtz shroud. In some embodi-ments, the field-coupling Helmholtz shroud (501) is made of a steel material which provides the proper acoustic imped-ance to promote enhancement of the leaf cell resonator (200) measurement sensitivities. The articulated deployment of the fluid sensors (52) depicted in FIGS. 2A-3C allows characterization of the flow properties distribution over the wellbore cross-section in highly deviated and horizontal wellbores under the entire range of inhomogeneous flows that can occur downhole. As described in reference to FIGS. 6A-6G below, the leaf cell resonator (200) provides simul-taneous and congruent measurement of fluid density and sound speed for downhole multiphase compositional analy-sis involving gas saturated two-phase fluids.

Measurement of one or more rheological properties of a fluid may allow determination of other properties, for example, the composition of the fluid. Acoustic measure-ments can be used for determining composition and chemi-cal properties of unknown fluids, for example, multi-phase fluids, and may be applied to fluid identification (ID) prob-lems in a variety of sensor development fields. Without wishing to be bound by theory, certain chemometric corre-lations may exist between downhole multi-phase fluid prop-erties and bulk fluid acoustic properties, for example, of sound speed and density. Example downhole multi-phase fluid properties include volume fractions, gas-oil-ratio (GOR), American Petroleum Institute oil gravity (API) (where API gravity=141.5/SG−131.5, where SG is the spe-cific gravity of crude oil), live-oil density, and live-oil compressibility. FIGS. 6A-6G below illustrate an example resonant cell geometry sensor that provides real-time bulk fluid acoustic properties measurements that may be part of a system and methods for multi-phase fluid decomposition analysis. Example sensors described in FIGS. 6A-6G may retrieve fluid property measurements, for example, of both continuous and dispersed phase, simultaneously and con-gruently, forming a basis for in situ and real-time multi-phase compositional analysis. In particular, the example leaf cell resonator sensor as described may provide simultaneous and congruent measurement of acoustic properties that may allow in situ downhole discrimination of bulk fluid proper-ties, for example, mass density and sound speed. An example fluid may be a multi-phase fluid. An example fluid may include oil, water, gas, drilling fluid, or a combination of two or more of oil, water, gas, and drilling fluid. An example resonator sensor implementation may use the dynamic acoustic behavior of a dilatational fluid volume brought into resonance by electromechanical means to form an algorithm that relates feedback coupling between the resonating fluid volume and the electromechanical device to infer acoustic properties of the fluid. The dilatational reso-nance of the fluid volume may be formed intrinsically by curvilinear Rhodonea contours of a leaf-type cell piezoelec-tric structure acting on a subdomain of a fluid that flows through the cell structure to create an intrinsic Helmholtz cavity response, for example, using only the leaf cell and the fluid.

Figure 6A:
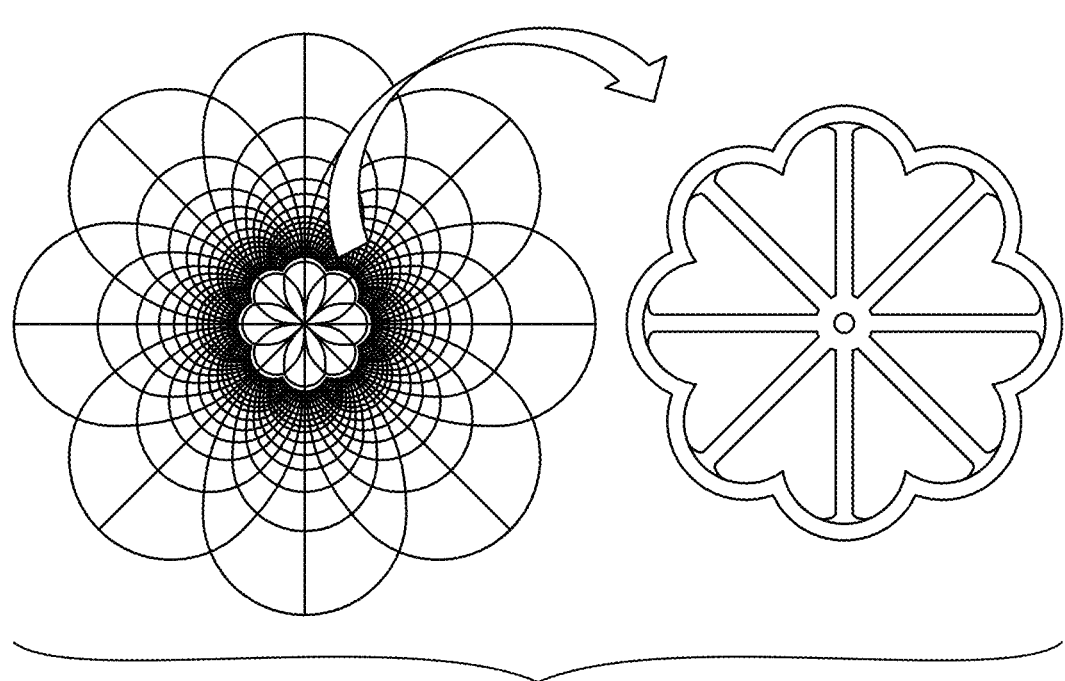
FIG. 6A shows a graphical representation of a Rhodonea cell resonator geometry based on conformal mapping contours in accordance with one or more embodiments.

FIG. 6A shows a graphical representation of an example Rhodonea cell resonator geometry based on conformal map-ping contours. The geometry for an example leaf cell resonator element may be based on contour segments of the canonical Rhodonea conformal mapping geometry defined by the mathematical relations:

$$x = \pm \frac{1}{\rho} \sqrt{\rho + u} \qquad \text{Eq. (1)}$$

$$y = \pm \frac{1}{\rho} \sqrt{\rho - u} \qquad \text{Eq. (2)}$$

$$\rho = \sqrt{u^2 + v^2} \qquad \text{Eq. (3)}$$

Where 'u' and 'v' are the are the Rhodonea conformal domain coordinates as illustrated in the constant coordinate 'x'/'y' plot of FIG. 6A, and p designates a variable function of the two mapping variables 'u' and 'v'. The conformal contour segments form an eight-fold symmetry in the leaf cell resonator geometry and are joined by eight central spoke members.

Figure 6B:
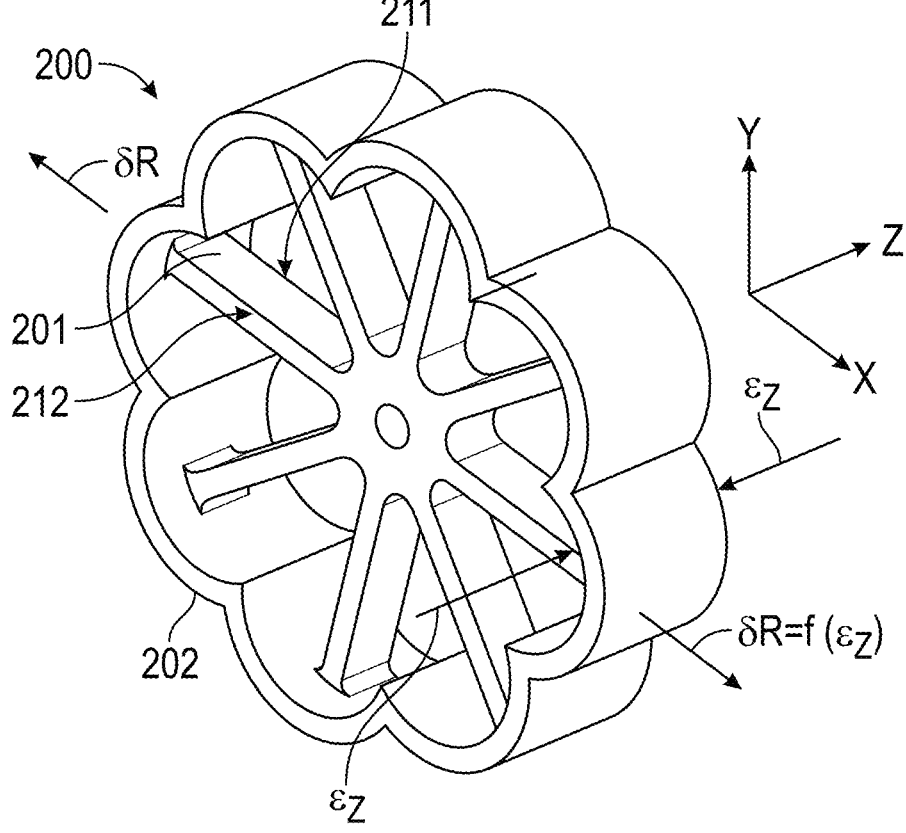
FIG. 6B shows a perspective view of an example leaf cell in accordance with one or more embodiments.

An example leaf cell (200) is shown in FIG. 6B. In some implementations, a leaf resonator is excited by applying an electrical voltage potential across electrically conductive electrode surfaces placed on the top and bottom faces (for example, proximal face (211) and distal face (212) of one or more central spoke members (201) as illustrated in FIG. 6B. The applied voltage creates a through-thickness mechanical strain (strain along the Z-axis, $\varepsilon_z$) in each spoke member due to the piezoelectricity of the leaf cell material, such as lead zirconate titanate. As a consequence of the Poisson's ratio effect (the negative of the ratio of transverse strain to axial strain), this through-thickness strain creates a corresponding longitudinal strain in each spoke member (201) in the radial direction (X-Y plane, δR) that results in symmetrical dilatation of the leaf cell resonator (202). Resonance excitation may therefore be developed by applying a harmonic electrical potential that creates a frequency response in the cell in which the eight curvilinear segments fold and unfold energetically to perform work on the fluid captured within the eight-fold contour boundary. In some implementations, a leaf cell may include 1, 2, 3, 4, 5, 6, 7, 8, 9, or (10) curvilinear segments. The instantaneous acoustic impedance of the fluid within the cell boundary may then detected as a change in the stress field within piezoelectric spoke members as evidenced, for example, as a change in the electrical current in the leaf cell electrodes and the integrated electrical circuit. The fluid properties may then be characterized, for example, by an instantaneous electrical admittance spectrum where changes in certain parameters of the admittance spectrum (for example, frequency, bandwidth, and shape) form the basis for a fluid identification measurement algorithm.

Electrical admittance is a measure of how easily a circuit or device will allow a current to flow and is defined as admittance Y=1/Z, where Z is the impedance. In reactive (alternating current) circuits, voltage V=IZ, where V and I are the complex scalars in the voltage and current respectively, and Z is the complex impedance. In Cartesian form, impedance is defined as Z=R+jX where the real part of impedance is the resistance R and the imaginary part is the reactance X (the opposition of a circuit element to a change in current or voltage). The mechanical deformation of a conductor (for example, a leaf cell) alters the resistance and reactance of the conductor, and a change in current (for example, phase shift or magnitude) flowing across the conductor may be detected and used to determine complex admittance spectra.

Figure 6C:
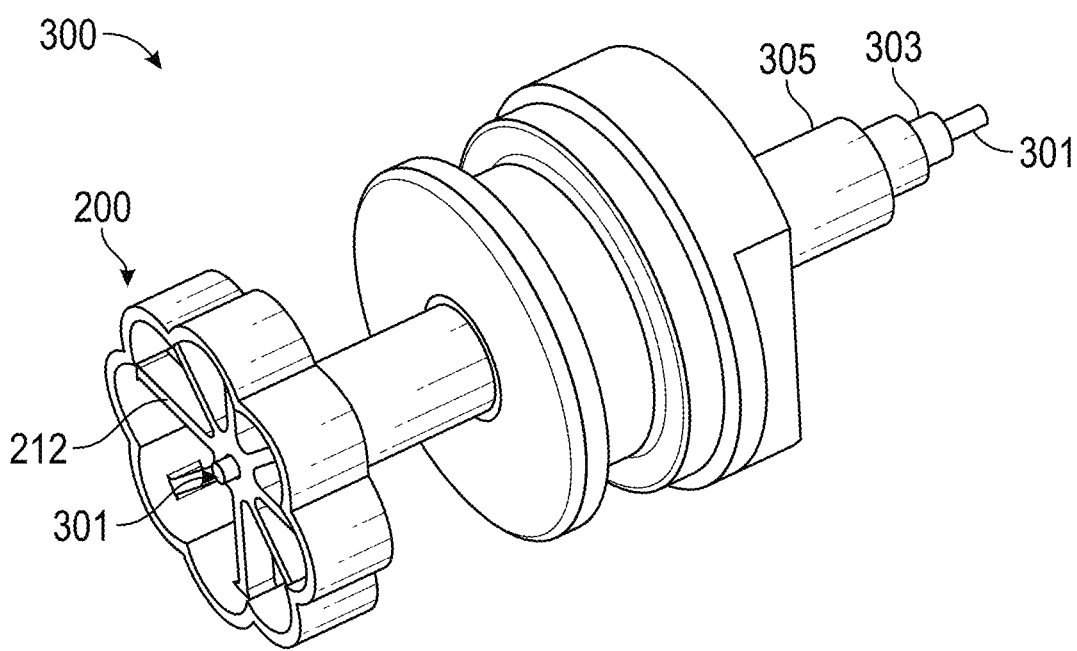
FIGS. 6C and 6D show perspective views of an example leaf cell sensor assembly in accordance with one or more embodiments.
Figure 6D:
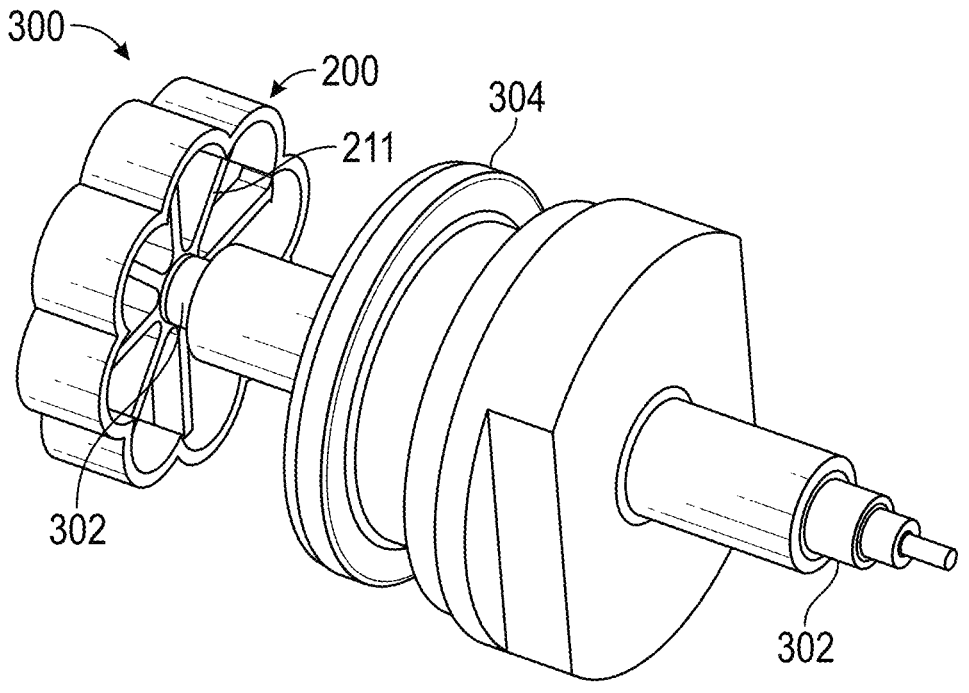
Figure 6G:
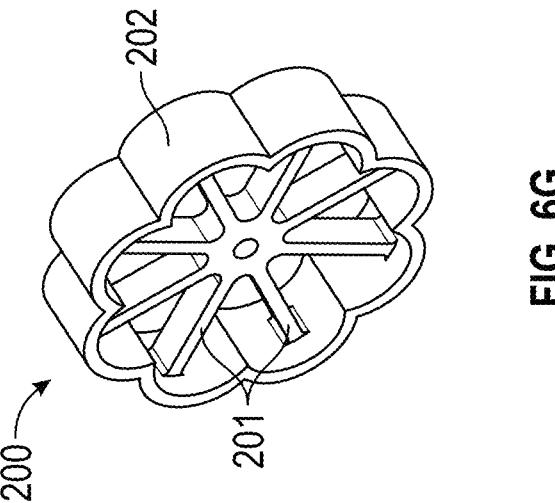
FIGS. 6E, 6F, and 6G show a frontal view, a cut-away side view, and a perspective view of an example leaf cell in accordance with one or more embodiments.
Figure 6F:
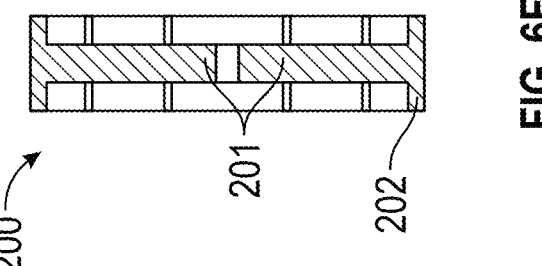
Figure 6E:
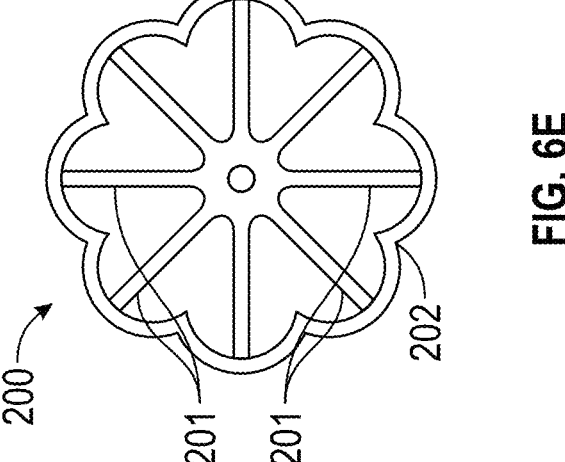

An example leaf cell sensor assembly design is illustrated in FIG. 6C and FIG. 6D. The design concept is based on a coaxial electrical feedthrough approach. An example sensor assembly (300) includes an example leaf cell (200) at a distal end of the assembly. An example leaf cell (200) may include one or more radial components (spokes) and a circumferential component (resonator) having a shape based on contour segments of the canonical Rhodonea conformal mapping geometry defined, for example, by the mathematical relations Eq. 1, Eq. 2, and Eq. 3 described in reference to FIG. 6A. A frontal view), a cut-away side view, and a perspective view of an example leaf cell (200) are shown in FIGS. 6E, 6F, and 6G, respectively. In some implementations, the outer diameter of a resonator is between 100 millimeters and 5 millimeters (mm). In some implementations, the outer diameter of a resonator is between 8 mm and (12) mm. In an example implementation, the outer diameter of a resonator is (10) mm. A leaf cell may include two or more electrodes that may be connected to an inner contact and an outer contact, respectively, for example, of a pressure feedthrough. In some implementation, an electrode may be placed on a spoke of the leaf cell. For example, an inner contact (301) may be connected to an electrode on a distal face (212) of a leaf cell (200), and an outer contact (302) may be connected to an electrode on a proximal face (211) of the leaf cell (200). In some implementations, example pressure feedthrough contacts may include one or more conducting elements that run along the length of a feedthrough assembly. An example inner contact (301) and an example outer contact (302) are otherwise insulated from each other, for example, by an inner insulator (303), such that current flows between the electrodes. Outer contact (302) may be insulated from one or more components (for example, a feedthrough housing (304) of the leaf cell sensor assembly (300) by outer insulator (305). The inner contact (301), outer contact (302), inner insulator (303), outer insulator (305), and feedthrough housing (304) collectively form a coaxial feedthrough connector, such as the sensor coaxial feedthrough connector (506) depicted in FIGS. 5A-5D above. The inner contact (301) and outer contact (302) of the example coaxial feedthrough connector may be connected to a voltage source, e.g., via a two-pin pressure feedthrough (507) depicted in FIGS. 5A-5D above. In some implementations, an inner contact may be connected to a negative terminal of the voltage source, and an outer contact may be connected to a positive terminal of the voltage source. In some implementations, an inner contact may be connected to a positive terminal of the voltage source, and an outer contact may be connected to a negative terminal of the voltage source. The voltage source is included within the electronics controller module that may be located at various places within the fluid analysis tool (40), so long as the location is isolated to prevent flooding of the module by wellbore fluids. For example, the voltage source may be located within the collar portion interior to the compression spring (43). In another example, the voltage source may be included in a separate electronics module tool that interfaces with the sensor assembly at either of the ends (44, 46). Electrodes and contacts may be connected to a leaf cell such that a voltage can be applied across the thickness of the leaf cell spokes, for example, spokes (201). An inner contact and an outer contact may be connected to an electric current measurement device, for example, an ammeter, to measure current across the thickness of a leaf cell, for example, leaf cell (200).

In some implementations, one or more components of a leaf cell sensor may be adapted to a variety of downhole fluid identification applications including production logging, logging while drilling, and formation sampling and testing. A leaf cell sensor may be implemented as a standalone device or may be integrated into one or more downhole tools, for example, production logging or logging while drilling tools such as the downhole tool measurement module (28) and the fluid analysis tool (40) described in reference to FIGS. 1-3C above.

An example leaf cell sensor operates on the principle that upon excitation of the leaf cell a nearly uniform cylindrical shaped pressure distribution is developed throughout an interior fluid region encompassed by the leaf cell boundary, where the pressure distribution is that of a classical Helmholtz resonator cavity response, but without the reflective walls of a cavity. This aspect of the resonance response is an intent of design for the sensor to interact specifically with the bulk modulus of a fluid medium, and subsequently provide sensitivity to changes in the fluid properties, for example, density and sound speed from, for example, the compressibility of the fluid. As a result, a unique feature of the leaf cell resonator sensor is that the sensor is capable of retrieving fluid measurements, for example, a density or sound speed measurement, or both from the fluid independent of the method of deployment, as there is no need for extraneous boundaries in order to develop the Helmholtz cavity-type response. In effect, the resonance characteristics of the fluid volume are coupled intrinsically to the dynamics of the set of curvilinear Rhodonea contour arcs and spoke members comprising the leaf-type cell piezoelectric structure, for example, through the dynamic compressibility of the fluid.

Figure 7A:
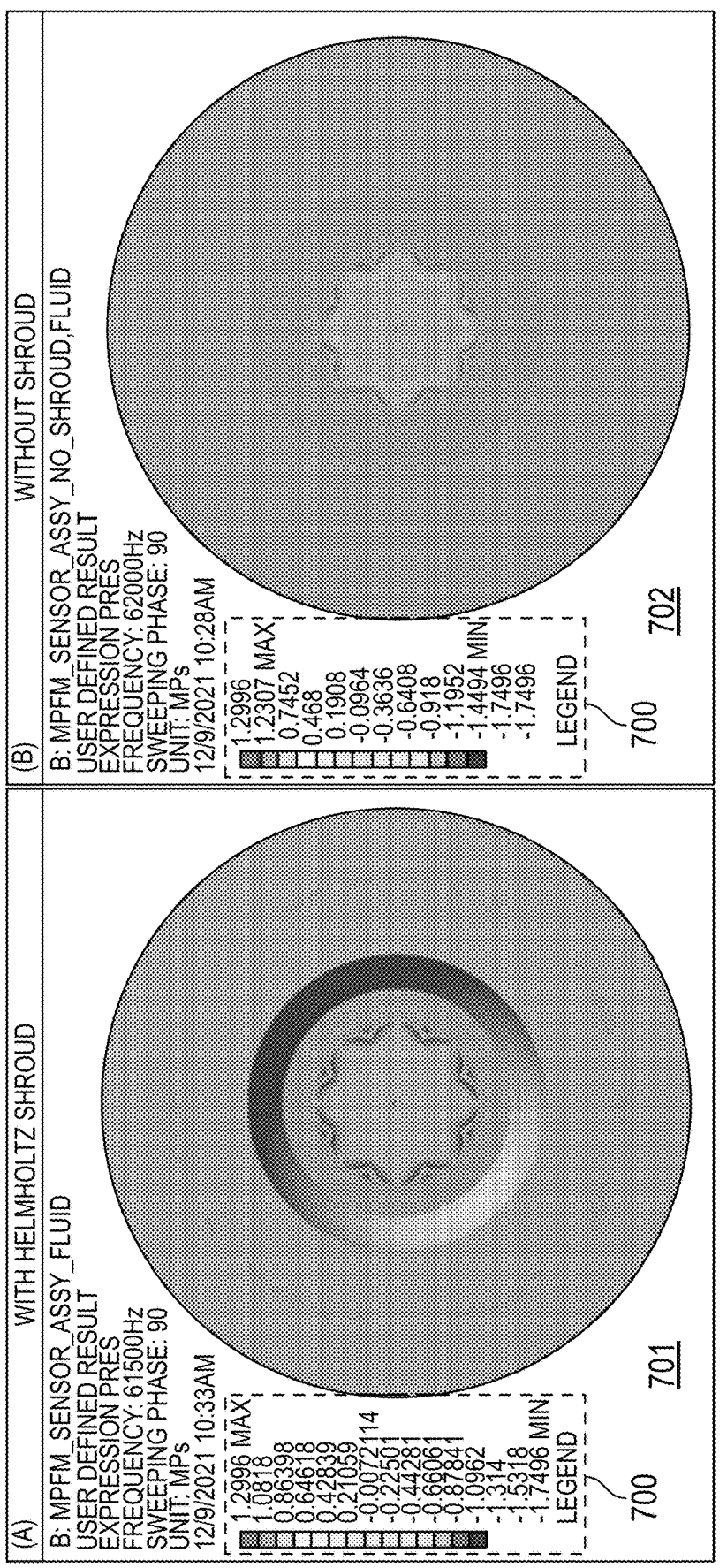
FIG. 7A shows example leaf cell sensor acoustic pressure fields in accordance with one or more embodiments.

FIG. 7A shows example plots of the leaf cell sensor acoustic pressure fields in accordance with one or more embodiments. As shown in FIG. 7A, the leaf cell sensor acoustic pressure field (701) corresponds to the fluid sensor (52) where the sensor assembly (300) includes the leaf cell (200) with field-coupling Helmholtz cavity shroud (501) as depicted in FIGS. 5A-5D. In particular, the exterior metal Helmholtz cavity wall (502) couples the leaf cell (200) intrinsic interior Helmholtz resonator response with the leaf cell external acoustic field (701). In contrast, the leaf cell sensor acoustic pressure field (702) corresponds to the fluid sensor (52) with the field-coupling Helmholtz cavity shroud (501) removed. For both acoustic fields (701) and (702), each of the two-dimensional plots correspond to a cross-section of the fluid sensor (52) while each origin of the plots correspond to the central axis of the fluid sensor (52). The integration of the field-coupling Helmholtz cavity shroud (501) increases the amplitude (depicted according to the legend (700)) of the leaf cell pressure field (701) over the leaf cell pressure field (701) by approximately 15%.

Figure 7B:
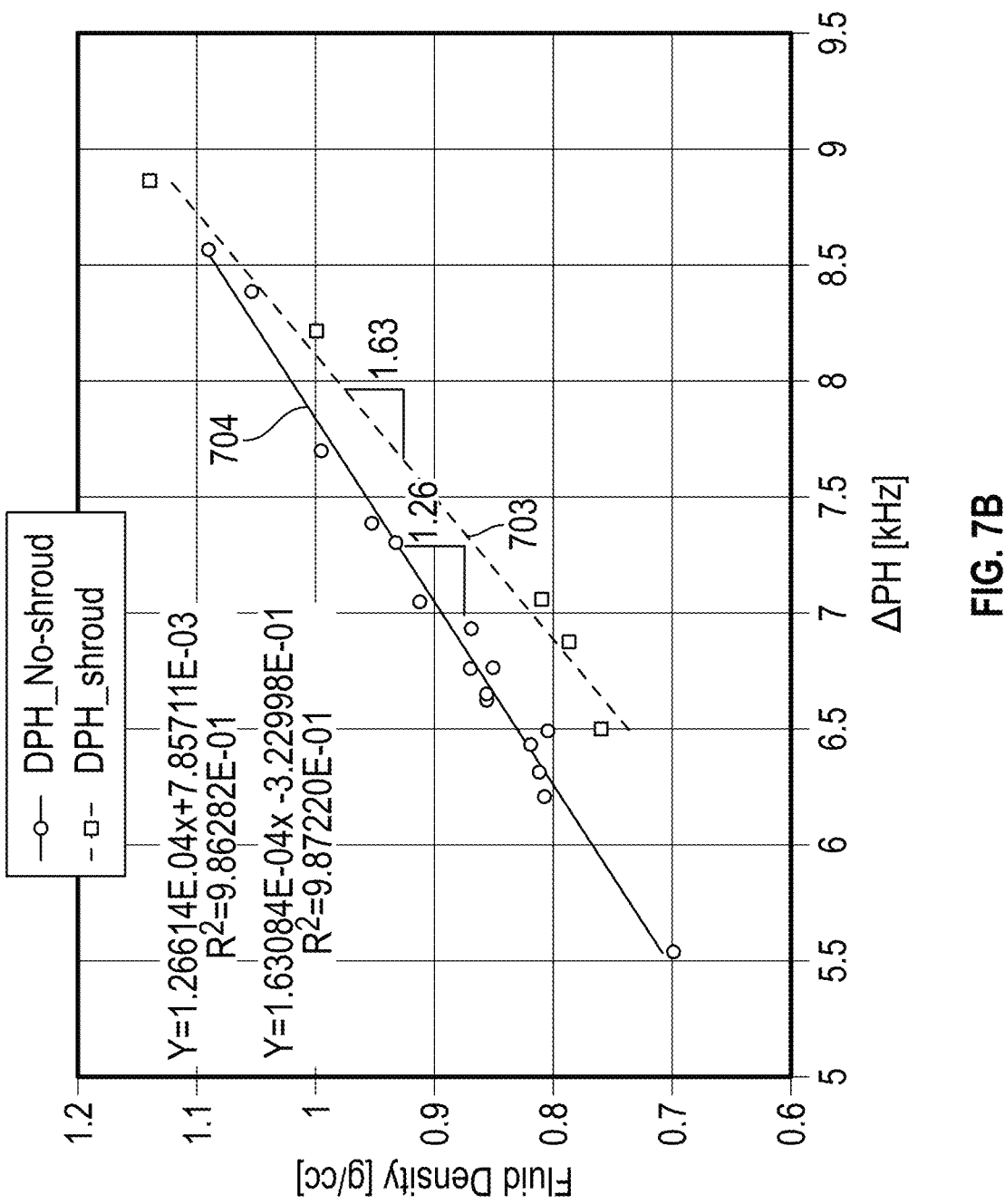
FIG. 7B shows example leaf cell sensor fluid density sensitivities in accordance with one or more embodiments.

FIG. 7B shows example leaf cell sensor fluid density measurement sensitivities in accordance with one or more embodiments. As shown in FIG. 7B, the leaf cell sensor fluid density sensitivity (703) corresponds to the fluid sensor (52) where the sensor assembly (300) includes the leaf cell (200) with field-coupling Helmholtz cavity shroud (501) as depicted in FIGS. 5A-5D. In contrast, the leaf cell sensor fluid density sensitivity (704) corresponds to the fluid sensor (52) with the field-coupling Helmholtz cavity shroud (501) removed. The integration of the field-coupling Helmholtz cavity shroud (501) increases the sensitivity of the leaf cell pressure field (701) over the leaf cell pressure field (701) by approximately 30%. FIG. 7B illustrates the frequency change (APH) of the leaf cell resonator admittance phase spectrum with changes in the density of the fluid surrounding the resonator. The comparison shows approximately $1.266 \times 10^{-4}$ (g/cc)/Hz density sensitivity for the baseline design without the shroud and approximately $1.63 \times 10^{-4}$ (g/cc)/Hz density sensitivity with the field-coupling Helmholtz cavity shroud included in the sensor assembly (300) of the fluid sensor (52).

While the disclosure has been described with respect to a limited number of embodiments, those skilled in the art, having benefit of this disclosure, will appreciate that other embodiments can be devised which do not depart from the scope of the disclosure as disclosed herein. Accordingly, the scope of the disclosure should be limited only by the attached claims.

What is claimed:

1. A fluid analysis tool for measuring one or more properties of a fluid, comprising:
   an axial spring; and
   a plurality of arms movable, in response to extension of the axial spring, from a retracted position into an expanded position, each arm comprising at least one fluid sensor device for measuring the one or more properties of the fluid,
      wherein the plurality of arms is fixed at opposing ends and bendable at a location between the opposing ends,
      wherein the plurality of arms is arranged about a central axis, and
      wherein the plurality of arms expands away from the central axis to position into the expanded position and contracts towards the central axis to position into the retracted position,
   wherein the at least one fluid sensor device comprises:
      a leaf cell sensor comprising a piezoelectric structure acting on a subdomain of the fluid that flows through the piezoelectric structure to create an intrinsic Helmholtz cavity response; and
      an enclosure enclosing the leaf cell sensor and comprising:
         a flowthrough shroud comprising:
            an inlet that allows the fluid to enter the enclosure and pass across the leaf cell sensor; and
            a Helmholtz cavity wall that couples the intrinsic Helmholtz cavity response with an external acoustic field of the leaf cell sensor to increase a measurement sensitivity of the at least one fluid sensor device;
         a cylindrical housing comprising:
            an outlet that allows the fluid to exit the enclosure; and
            a pressure feedthrough connector that transmits an electrical signal induced by the intrinsic Helmholtz cavity response from the piezoelectric structure of the leaf cell sensor,
   wherein the at least one fluid sensor device is mounted on a Stephenson six-bar mechanism of a respective arm among the plurality of arms,
   wherein the Stephenson six-bar mechanism maintains an orientation of the at least one fluid sensor device within ±3 degrees from an axis of a borehole as the plurality of arms move from the retracted position into the expanded position in response to the extension of the axial spring as the fluid analysis tool traverses the borehole, and
   wherein the electrical signal represents the one or more properties of the fluid.

2. The fluid analysis tool of claim 1, wherein the piezoelectric structure comprises:
   one or more piezoelectric radial components connected to a circumferential component, the one or more piezoelectric radial components and the circumferential component having a distal face and a proximal face;
   a first electrode positioned on the distal face of at least one radial component; and
   a second electrode positioned on the proximal face of the at least one radial component,
   wherein the electrical signal comprises an electric current flowing between the first electrode and the second electrode.

3. The fluid analysis tool of claim 1,
   wherein the at least one fluid sensor device is movable from a stored position to a deployed position relative to the respective arm on which the at least one fluid sensor device is located.

4. The fluid analysis tool of claim 1,
   wherein the at least one fluid sensor device is coupled to the respective arm via a pivot and configured to swing away from the respective arm towards the central axis of the fluid analysis tool.

5. The fluid analysis tool of claim 1, where the fluid analysis tool is integrated into a production logging tool or a logging while drilling tool.

6. A system for performing a wellbore operation, comprising:
   a wellbore penetrating a formation;
   a work string conveyed in the wellbore; and
   a fluid analysis tool suspended in the wellbore via the work string for measuring one or more properties of a fluid in the wellbore to facilitate the wellbore operation,
   wherein the fluid analysis tool comprises:
      an axial spring; and

15

16 a plurality of arms movable, in response to extension of the axial spring, from a retracted position into an expanded position, each arm comprising at least one fluid sensor device for measuring the one or more properties of the fluid, wherein the plurality of arms is fixed at opposing ends and bendable at least one location between the opposing ends, wherein the plurality of arms is arranged about a central axis, and wherein the plurality of arms expand away from the central axis to position into the expanded position and contract towards the central axis to position into the retracted position;

wherein the at least one fluid sensor device comprises:

a leaf cell sensor comprising a piezoelectric structure acting on a subdomain of the fluid that flows through the piezoelectric structure to create an intrinsic Helmholtz cavity response; and an enclosure enclosing the leaf cell sensor and comprising:

a flowthrough shroud comprising:

an inlet that allows the fluid to enter the enclosure and pass across the leaf cell sensor; and a Helmholtz cavity wall that couples the intrinsic Helmholtz cavity response with an external acoustic field of the leaf cell sensor to increase a measurement sensitivity of the at least one fluid sensor device;

a cylindrical housing comprising:

an outlet that allows the fluid to exit the enclosure; and a pressure feedthrough connector that transmits an electrical signal induced by the intrinsic Helmholtz cavity response from the piezoelectric structure of the leaf cell sensor, wherein the at least one fluid sensor device is mounted on a Stephenson six-bar mechanism of a respective arm among the plurality of arms, and wherein the Stephenson six-bar mechanism maintains an orientation of the at least one fluid sensor device within ±3 degrees from an axis of the wellbore as the plurality of arms move from the retracted position into the expanded position in response to the extension of the axial spring as the fluid analysis tool traverses the wellbore, and wherein the electrical signal represents the one or more properties of the fluid.

7. The system of claim 6, wherein the piezoelectric structure comprises:

one or more piezoelectric radial components connected to a circumferential component, the one or more piezoelectric radial components and the circumferential component having a distal face and a proximal face;

a first electrode positioned on the distal face of at least one radial component; and a second electrode positioned on the proximal face of the at least one radial component, wherein the electrical signal comprises an electric current flowing between the first electrode and the second electrode.

8. The system of claim 6, wherein the at least one fluid sensor device is movable from a stored position to a deployed position relative to the respective arm on which the at least one fluid sensor device is located.

9. The system of claim 6, wherein the at least one fluid sensor device is coupled to the respective arm via a pivot and configured to swing away from the respective arm towards the central axis of the fluid analysis tool.

* * * * *